United States Patent [19]

Varasi et al.

[11] Patent Number: 5,084,454
[45] Date of Patent: Jan. 28, 1992

[54] 2-(PIPERIDINYLMETHYL)-4-PHENYL-2,3-DIHYDRO-4H-1,4-BENZOXAZINES USEFUL AS ANTIPSYCHOTICS

[75] Inventors: Mario Varasi, Milan; Piero Melloni, Bresso; Maria A. Cervini, Cardano al Campo; Alberto Bonsignori, Milan; Roberto Commisso, Voghera, all of Italy

[73] Assignee: Farmitalia Carlo Erba S.r.l., Milan, Italy

[21] Appl. No.: 434,689

[22] PCT Filed: Feb. 13, 1989

[86] PCT No.: PCT/EP89/00130
§ 371 Date: Oct. 11, 1989
§ 102(e) Date: Oct. 11, 1989

[87] PCT Pub. No.: WO89/07596
PCT Pub. Date: Aug. 24, 1989

[30] Foreign Application Priority Data

Feb. 15, 1988 [GB] United Kingdom ............... 8803419

[51] Int. Cl.$^5$ .............. C07D 265/36; C07D 279/16; A61K 31/535; A61K 31/54
[52] U.S. Cl. ..................... 514/230.5; 544/6; 544/51; 544/70; 544/105
[58] Field of Search ............... 544/70, 105; 514/230.5

[56] References Cited

U.S. PATENT DOCUMENTS 3,058,980 10/1962 Berg ..................... 544/105

FOREIGN PATENT DOCUMENTS 0204148 12/1986 European Pat. Off. .
0233728 8/1987 European Pat. Off. .
2080791 2/1982 United Kingdom .

OTHER PUBLICATIONS

*Drug Evaluations*, 6th Edition, American Medical Association, Chicago, Ill., (1986), pp. 111-113.

*Primary Examiner*—Donald G. Daus
*Assistant Examiner*—Philip I. Dalton
*Attorney, Agent, or Firm*—Armstrong, Nikaido, Marmelstein, Kubovcik & Murray

[57] ABSTRACT

The present invention relates to compounds having the following formula (I)

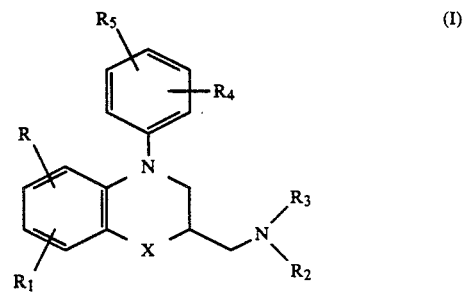

wherein
X represents —O— or —S—;
each of R and $R_1$, independently, is hydrogen, halogen, hydroxy, $C_1$–$C_6$ alkyl, $C_1$–$C_6$ alkoxy, amino, nitro or trihalo-$C_1$–$C_6$ alkyl;
each of $R_2$ and $R_3$, independently, is hydrogen, $C_1$–$C_6$ alkyl, $C_2$–$C_6$ alkenyl, $C_2$–$C_6$ alkynyl or phenyl-$C_1$–$C_6$ alkyl; or $R_2$ and $R_3$, taken together with the nitrogen atom to which they are linked, form an unsubstituted or substituted, 6-membered, saturated, heteromonocyclic ring optionally containing a further heteroatom chosen from oxygen, sulphur and nitrogen;
each of $R_4$ and $R_5$, independently, is hydrogen, halogen, nitro, amino or trihalo-$C_1$–$C_6$ alkyl; and the pharmaceutically acceptable salts thereof. The compounds of the invention are useful in therapy as major tranquilizers e.g., in the management of psychotic disorders.

17 Claims, No Drawings

2-(PIPERIDINYLMETHYL)-4-PHENYL-2,3-DIHYDRO-4H-1,4-BENZOXAZINES USEFUL AS ANTIPSYCHOTICS

DESCRIPTION

The present invention relates to substituted 4-aryl derivatives of 2,3-dihydro-4H-1,4-benzoxazine and 2,3-dihydro-4H-1,4-benzothiazine, to a process for their preparation, to pharmaceutical compositions containing them, and to their use in the preparation of pharmaceutical compositions having anti-psychotic activity.

Most of the classical drugs, up to now used in therapy for the management of psychotic disorders, act mainly on the dopaminergic pathways as dopamine antagonists. This pharmacological activity is closely associated with their antischizophrenic effects, in particular against symptoms, such as hallucinations and delusions. However the dopamine antagonists now available in therapy are meagrely effective against other symptoms of schizophrenia, such as apathy and withdrawn social behaviour, and unfortunately are associated with extrapyramidal side effects. Therefore in therapy remains a strong need of drugs active in treating also these latter aspects of the psychotic syndrome, and having no, or negligible, neurological side effects.

The invention provides compounds having the following general formula (I)

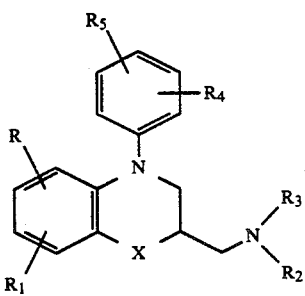

(I)

wherein
X represents —O— or —S—;
each of R and $R_1$, independently, is hydrogen, halogen, hydroxy, $C_1-C_6$ alkyl, $C_1-C_6$ alkoxy, amino, nitro or trihalo-$C_1-C_6$ alkyl;
each of $R_2$ and $R_3$, independently, is hydrogen, $C_1-C_6$ alkyl, $C_2-C_6$ alkenyl, $C_2-C_6$ alkynyl or phenyl-$C_1-C_6$ alkyl; or $R_2$ and $R_3$, taken together with the nitrogen atom to which they are linked, form an unsubstituted or substituted, 6-membered, saturated, heteromonocyclic ring optionally containing a further heteroatom chosen from oxygen, sulphur and nitrogen;
each of $R_4$ and $R_5$, independently, is hydrogen, halogen, nitro, amino or trihalo-$C_1-C_6$ alkyl; and the pharmaceutically acceptable salts thereof.

The invention also includes within its scope all the possible isomers, stereoisomers and optical isomers and their mixtures, and the metabolites and the metabolic precursors or bio-precursors of the compounds of formula (I).

A halogen atom is e.g. chlorine, bromine or fluorine, preferably it is fluorine.

The alkyl, alkenyl, alkynyl and alkoxy groups may be branched or straight chain groups. A $C_1-C_6$ alkyl group is preferably a $C_1-C_4$ alkyl group, e.g. methyl, ethyl, propyl, isopropyl, butyl, sec. butyl or tert. butyl, more preferably it is methyl or ethyl. A $C_2-C_6$ alkenyl group is preferably a $C_2-C_4$ alkenyl group, in particular allyl. A $C_2-C_6$ alkynyl group is preferably a $C_2-C_4$ alkynyl group, in particular propargyl.

A phenyl-$C_1-C_6$ alkyl group is preferably a phenyl-$C_1-C_4$ alkyl, in particular benzyl or phenethyl.

A $C_1-C_6$ alkoxy group is preferably a $C_1-C_4$ alkoxy group, e.g. methoxy, ethoxy, propoxy, isopropoxy, butoxy or tert.butoxy, more preferably it is methoxy or ethoxy.

A trihalo-$C_1-C_6$ alkyl group is preferably a trihalo-$C_1-C_4$ alkyl group, e.g. trichloro-$C_1-C_4$ alkyl or trifluoro-$C_1-C_4$ alkyl, more preferably it is trifluoromethyl.

When $R_2$ and $R_3$, taken together with the nitrogen atom to which they are linked, form an heteromonocyclic ring as defined above, it may be for example a ring chosen from the group including piperidine, piperazine, morpholine or thiomorpholine, which may be unsubstituted or substituted at one or two carbon atoms by one or two substituents independently chosen from the group including:

a) hydroxy and $C_1-C_6$ alkyl;
b) phenyl unsubstituted or substituted by one to three substituents independently chosen from hydroxy, halogen, $C_1-C_6$ alkyl, $C_1-C_6$ alkoxy and trifluoro-methyl;
c) 2-keto-1-benzoimidazolinyl; and
d) 1-phenyl-4-keto-5-imidazolidinyl, so as to provide e.g. a 1-phenyl-1,3,8-triazaspiro[4,5]decan-4-one condensed ring system, i.e.

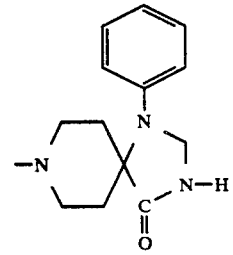

in which the phenyl ring is unsubstituted or substituted by one to three substituents chosen independently from hydroxy, halogen, $C_1-C_6$ alkyl and trifluoromethyl, and the nitrogen atom at the 1-position of the imidazolidine ring may be unsubstituted or substituted by $C_1-C_6$ alkyl, phenyl or by phenyl-$C_1-C_6$ alkyl.

When $R_2$ and $R_3$, taken together with the nitrogen atom to which they are linked, form an heterocyclic ring, as defined above, which contains a further nitrogen atom, the additional nitrogen atom may be unsubstituted or substituted by a substituent chosen from the group including $C_1-C_6$ alkyl, pyridyl and pyrazinyl or by phenyl unsubstituted or substituted by one to three substituents chosen from hydroxy, halogen, $C_1-C_6$ alkyl, $C_1-C_6$ alkoxy and trifluoromethyl.

When $R_2$ and $R_3$, taken together with the nitrogen atom to which they are linked, form an heterocyclic ring as defined above, preferably it is selected from the group including:

a') unsubstituted morpholine;
b') piperazine unsubstituted or substituted by pyridyl, pyrazinyl or by phenyl unsubstituted or substituted by one or two substituents independently chosen from halogen, trifluoromethyl, $C_1-C_4$ alkyl and $C_1-C_4$ alkoxy; and c') piperidine unsubstituted or substituted by one or two substituents chosen independently from hydroxy, 2-keto-1-benzoimidazolinyl and phenyl unsubstituted or substituted by halogen; or the piperidine ring may be substituted by 1-phenyl-4-keto-5-imidazolindinyl.

The pharmaceutically acceptable salts of the compounds of formula (I) include those formed with an inorganic acid, e.g. nitric acid, hydrochloric acid or sulphuric acid, or with an organic acid, e.g. citric, malic, maleic, mandelic, tartaric, fumaric or methane-sulphonic acid.

As stated above, the present invention also includes within its scope pharmaceutically acceptable bioprecursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are the compounds of formula (I), wherein

X represents —O— or —S—;

each of R and $R_1$, independently, is hydrogen, halogen, hydroxy, amino, $C_1$-$C_4$ alkyl, $C_1$-$C_4$ alkoxy, trifluoromethyl or nitro;

each of $R_2$ and $R_3$, independently, is hydrogen or $C_1$-$C_4$ alkyl, or $R_2$ and $R_3$, taken together with the nitrogen atom to which they are linked, form a heteromonocyclic ring chosen from a") unsubstituted morpholine;

b") piperazine unsubstituted or substituted by pyridyl, pyrazinyl or by phenyl, the phenyl group being unsubstituted or substituted by one or two substituents independently chosen from halogen, trifluoromethyl, $C_1$-$C_4$ alkyl and $C_1$-$C_4$ alkoxy; and c") piperidine unsubstituted or substituted by one or two substituents chosen independently from hydroxy, 2-keto-1-benzoimidazolinyl, 1-phenyl-4-keto-5-imidazolidinyl and phenyl unsubstituted or substituted by one or two substituents chosen from halogen and trifluoromethyl;

$R_4$ is hydrogen;

$R_5$ is hydrogen, halogen or trifluoromethyl; and the pharmaceutically acceptable salts thereof.

More preferred compounds of the invention are the compounds of formula (I), wherein X represents —O—;

each of R and $R_1$, independently, is hydrogen, halogen or tri-fluoromethyl;

$R_2$ and $R_3$, taken together with the nitrogen atom to which they are linked, form a''') a piperidine ring unsubstituted or substituted by one or two substituents chosen from hydroxy, 2-keto-1-benzoimidazolinyl, 1-phenyl-4-keto-5-imidazolidinyl and phenyl unsubstituted or substituted by one or two substituents chosen from halogen and trifluoromethyl; or b''') a piperazine ring unsubstituted or substituted by unsubstituted pyridyl or by phenyl unsubstituted or substituted by one or two substituents chosen independently from halogen and $C_1$-$C_4$ alkoxy;

$R_4$ is hydrogen;

$R_5$ is hydrogen, halogen or trifluoromethyl, and the pharmaceutically acceptable salts thereof.

Examples of particularly preferred compounds of the invention are the following:

2-[4-(4-fluorophenyl)-4-hydroxy-piperidin-1-yl]-methyl-4-phenyl-2,3-dihydro-4H-1,4-benzoxazine;

2-[4-(2-methoxyphenyl)-piperazin-1-yl]-methyl-4-phenyl-2,3-dihydro-4H-1,4-benzoxazine;

2-(1-phenyl-1,3,8-triazaspiro[4,5]decan-4-one-8-yl)-methyl-4-phenyl-2,3-dihydro-4H-1,4-benzoxazine;

2-(1-phenyl-1,3,8-triazaspiro[4,5]decan-4-one-8-yl)-methyl-4-phenyl-7-fluoro-2,3-dihydro-4H-1,4-benzoxazine;

2-(1-phenyl-1,3,8-triazaspiro[4,5]decan-4-one-8-yl)-methyl-4-(4-fluorophenyl)-2,3-dihydro-4H-1,4-benzoxazine;

2-(1-phenyl-1,3,8-triazaspiro[4,5]decan-4-one-8-yl)-methyl-4-(4-fluorophenyl)-7-fluoro-2,3-dihydro-4H-1,4-benzoxazine;

2-[4-(3-trifluoromethyl-phenyl)-4-hydroxy-piperidin-1-yl]-methyl-4-phenyl-2,3-dihydro-4H-1,4-benzoxazine;

2-[4-(3-trifluoromethyl-phenyl)-4-hydroxy-piperidin-1-yl]-methyl-4-(4-fluorophenyl)-2,3-dihydro-4H-1,4-benzoxazine;

2-[4-(3-trifluoromethyl-phenyl)-4-hydroxy-piperidin-1-yl]-methyl-4-phenyl-7-fluoro-2,3-dihydro-4H-1,4-benzoxazine; and 2-[4-(3-trifluoromethyl-phenyl)-4-hydroxy-piperidin-1-yl]-methyl-4-(4-fluorophenyl)-7-fluoro-2,3-dihydro-4H-1,4-benzoxazine; in particular in the form of single enantiomers, and the pharmaceutically acceptable salts thereof.

The compounds of the invention and the salts thereof can be prepared by a process comprising reacting a compound of formula (II)

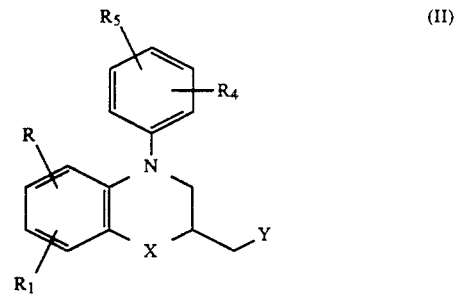

wherein

X, R, $R_1$, $R_4$ and $R_5$ are as defined above and Y represents the residue of a reactive ester or halogen, with a compound of formula (III)

wherein $R_2$ and $R_3$ are as defined above, and, if desired, converting a compound of formula (I) into another compound of formula (I), and/or, if desired, salifying a compound of formula (I), and/or, if desired, obtaining a free compound of formula (I) from a salt thereof, and/or, if desired, separating a mixture of isomers of compounds of formula (I) into the single isomers.

When Y is the residue of a reactive ester, it is preferably a sulphonate group, more preferably -O-mesyl or -O-tosyl. When Y is halogen, it is preferably chlorine or bromine.

The reaction between a compound of formula (II) and an amine of formula (III) may be carried out for example in an organic solvent such as dimethylformamide, dimethylacetamide, hexamethylphosphortriamide, tetrahydrofuran, dioxane or 1,2-dimethoxyethane, in the presence of an inorganic base, e.g. an alkali metal carbonate, preferably potassium carbonate, at temperatures generally from about 20° C. to the reflux temperature of the solvent used, with reaction times generally from about 1 hour to about 10 hours.

Alternatively to the inorganic base, an excess of the amine of formula (III) involved in the reaction may be added.

A compound of formula (I) may be converted, as stated above, into another compound of formula (I) by known methods. For example, a free hydroxy group may be etherified by reaction with a suitable alkyl halide in the presence of a base such as NaOH, KOH, $Na_2CO_3$, $K_2CO_3$, NaH, $NaNH_2$, sodium methoxide or sodium ethoxide in a solvent selected from the group consisting, for example, of methanol, ethanol, dioxane, acetone, dimethylformamide, hexamethylphosphorotriamide, tetrahydrofuran, water and their mixtures at a temperature ranging preferably between about 0° C. and about 150° C. Furthermore an etherified hydroxy group may be converted into a free hydroxy group, for example, by treatment with pyridine hydrochloride or with a strong acid such as HBr or HI, or with a Lewis acid such as $AlCl_3$ or $BBr_3$ or with an alkaline salt of a thiol.

Also the optional salification of a compound of formula (I) as well as the conversion of a salt into the free compound and the separation of a mixture of isomers into the single isomers may be carried out by conventional methods.

For example, the separation of a mixture of optical isomers into the individual isomers may be carried out by salification with an optically active acid and subsequent fractional crystallization or by esterification with an optically active acid derivative and separation of the diastereoisomers.

Thus, the separation of a mixture of geometric isomers may be carried out, for example, by fractional crystallization or by separation on column chromatography.

In the processes described in the specification, when required, reactive functional groups may be protected with suitable protecting reagents, which may be removed after the reaction by known methods, which are available from the chemical literature.

The compounds of formula (II) wherein Y is the residue of a reactive ester, e.g. an -O-mesyl or -O-tosyl group, may be prepared for example by reacting a compound of formula (IV)

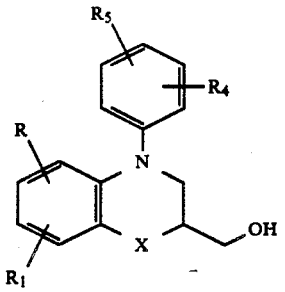

(IV)

wherein X, R, $R_1$, $R_4$ and $R_5$ are as defined above, with a suitable acyl, preferably sulphonyl, halide, preferably chloride, e.g. with p-toluene-sulphonylchloride or methanesulphonylchloride operating for instance in anhydrous pyridine at room temperature or in a solvent chosen from methylene chloride or chloroform, in the presence of an organic base, e.g. triethylamine, at a temperature ranging from about $-5°$ C. to about 20° C.

The compounds of formula (II) wherein Y represents halogen may be obtained for example from a compound of formula (IV), as defined above, through known methods, e.g. by treatment with $SOCl_2$ by conventional methods of organic chemistry, optionally in the presence of a suitable catalyst, for example $ZnCl_2$, or by treatment with $SOCl_2$ or oxalic acid dichloride in dimethylformamide, through the formation of a Vilsmeier reagent.

The compounds of formula (IV) may be obtained by reducing a compound of formula (V)

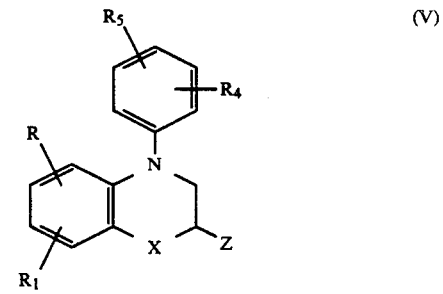

(V)

wherein, X, R, $R_1$, $R_4$ and $R_5$ are as defined above and Z represents a free, salified or esterified carboxy group.

When, in a compound of formula (V), Z is a salified carboxy group, the salt may be either a salt of an organic base or a salt of an inorganic base; preferably it is an alkali metal salt.

When, in a compound of formula (V), Z is an esterified carboxy group, the ester may be, for example, an alkyl ester; preferably it is a $C_1$–$C_6$ alkoxycarbonyl group, in particular methoxy- or ethoxy-carbonyl. The reduction of a compound of formula (V), wherein Z is esterified carboxyl, to give a compound of formula (IV), may, for example, be carried out using sodium borohydride as reducing agent in a solvent such as methanol, ethanol or isopropanol or a mixture of one of these solvents with water in ratios which vary depending on the solubility of the starting product; the said reduction may also be performed, e.g. using lithium aluminium hydride in inert solvents such as anhydrous diethyl ether or anhydrous tetrahydrofuran at temperatures which, in both cases, range from approximately 0° C. to the solvent reflux temperature, for reaction times ranging approximately between 30 minutes and 24 hours.

The reduction of a compound of formula (V) wherein Z represents a free carboxyl group, to give a compound of formula (IV), is preferably carried out using lithium aluminium hydride in inert solvents such as anhydrous ethyl ether, anhydrous diethylene glycol dimethyl ether, anhydrous tetrahydrofuran or mixtures thereof, or using preformed solutions of boron hydride in the aforesaid anhydrous solvents, or boron hydride prepared in situ in the reaction medium from sodium boronhydride and boron trifluoride etherate, preferably in diethylene glycol dimethyl ether, at temperatures ranging from about 0° C. to the solvent reflux temperature, for reaction times ranging approximately between 30 minutes and 12 hours.

The reduction of a compound of formula (V) wherein Z represents a salified carboxy group, to give a compound of formula (IV), is preferably carried out in conditions analogous to those employed in the reduction of a compound of formula (V) wherein Z is a free carboxy group.

The compounds of formula (V) wherein Z is an esterified carboxy group may be obtained through N-arylation of a compound of formula (VI)

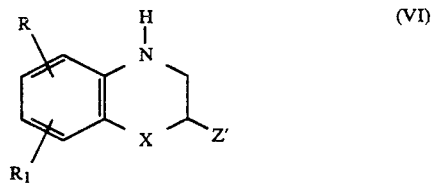

wherein X, R and $R_1$ are as defined above and Z' is an esterified carboxy group as defined above for Z. N-arylation of a compound of formula (VI) may be carried out by treatment with a phenyl derivative of formula (VII)

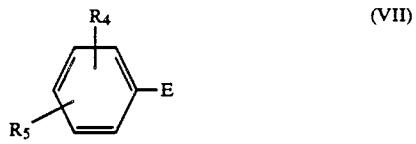

wherein $R_4$ and $R_5$ are as defined above and E is preferably a halogen atom, e.g. bromine or iodine, at a temperature ranging from about 50° C. to about 260° C., in the presence of copper or a suitable salt thereof e.g. CuI or CuBr and, if required, in a pressure vessel.

When a compound of formula (V) is required, wherein $R_4$ and $R_5$ are both hydrogen, N-arylation of a compound of formula (VI) may be performed to advantage by treatment with 1,4-cyclohexanedione in the presence of paratoluenesulfonic acid, in an aromatic hydrocarbon, preferably benzene or toluene, at reflux temperature, with contemporaneous removal of water by azeotropic distillation.

A compound of formula (V), wherein Z is a free or salified carboxy group, may be obtained according to known methods from a compound of formula (V), wherein Z is an esterified carboxy group.

The compounds of formulae (III) and (VI) are known and/or may be obtained according to known methods from known compounds.

As is clear from the relevant chemical structures, besides the compounds of formula (I), also the compounds of formula (II), (IV), (V) and (VI) are chiral molecules, in which the C-2 carbon atom is asymmetric; therefore they may exist as single optical isomers (enantiomers) or as a mixture thereof. When a compound of formula (I), in the form of single pure optical isomer is desired, it can be obtained either by resolving a mixture of its optical isomers into the single optical isomers, as described above, or by using a compound of formula (II), (IV), (V) or (VI), in the form of single optical isomer, as intermediate or starting material, respectively, in the process herein described.

In a preferred embodiment of the process according to the present invention, when a compound of formula (I), as single pure optical isomer is desired, a pure optical isomer of a compound of formula (V) is used as intermediate compound in such process.

The separation of a mixture of optical isomers of a compound of formula (V) into the individual isomers may be carried out by following the same method described above for separing a mixture of optical isomers of a compound of formula (I) into the single optical isomers. In particular a compound of formula (V), in which Z is a free carboxy group can be salified with an optically active base, e.g. ephedrine, and submitted to subsequent fractional crystallization.

A further object of the present invention are the intermediate compounds of formula (V)

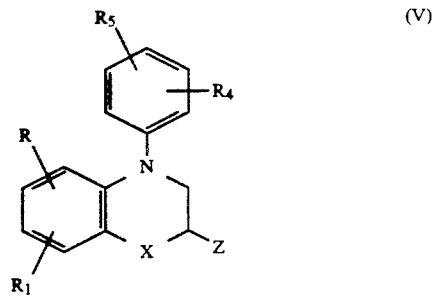

wherein X, R, $R_1$, $R_4$, $R_5$ and Z are as defined above, both in the form of single optical isomers and in the form of a mixture thereof, which are new.

The compounds of the invention are active on the central nervous system (CNS), in particular as CNS depressant, i.e. as major tranquilizers (neuroleptics) and can be used in therapy e.g. in the management of psychotic disorders and manic-depressive states, for the control of nausea and vomiting, for the treatment of restlessness and apprehension prior to surgery, post-surgical psychosis, excessive anxiety, post-miocardial infarction agitation, behavioural symptoms during intensive care and in AIDS patients with delirium and dementia. Moreover, by virtue of their high antidopaminergic properties, associated with low cataleptoenic activity, and of their potent activity in inhibiting the serotonin $5HT_2$ receptor binding, the compounds according to the present invention are active also in treating some symptoms of schizophrenia, which are meagrely sensitive to the therapeutical means now available, such as apathy and withdrawn social behaviour, and have no, or negligible, neurological side-effects.

The activity of the compounds of the present invention was evaluated for example in a series of receptorial binding affinity tests.

Table 1 shows for instance the binding affinity test data of a representative group of compounds according to the instant invention for $D_1$ and $D_2$ dopamine, $5HT_1$ and $5HT_2$ serotonine and $\alpha_1$ and $\alpha_2$ nor-adrenaline receptors, obtained according to well known procedures [Creese, I, Schneider, R, Synder, S. H. Europ. J. Pharmacol. 1977, 46, 377; Hyttel, J. Life Sci. 1981, 28, 563; Pedigo et al. Journal of Neurochemistry, 1981, 36, 220; Leysen et al. Molecular Pharmacology, 1981, 21, 301; Battaglia et al. Life Science, 1983, 33, 2011; Greengrass P., Brener R. Eur. J. Pharmacol., 1979, 55, 323; and Perry B. D., U'Prichard D. C. Eur. J. Pharmacol. 1981, 76, 461]

TABLE 1

| Compound | D$_1$ [3$_H$]cisFlu. | D$_2$ [3$_H$]Spip. | 5HT$_1$ [3$_H$]Serot. | 5HT$_2$ [3$_H$]Ket. | α$_1$ [3$_H$]Praz. | α$_2$ [3$_H$]Yohlm. |
|---|---|---|---|---|---|---|
| FCE 25456 | >10 | 0.001 | >10 | 0.1 | 0.4 | >10 |
| FCE 24867 | 1.4 | 0.008 | >10 | 0.04 | 0.1 | 1.7 |
| FCE 25895 | 1.2 | 0.005 | >10 | 0.006 | 0.08 | 0.8 |
| FCE 25896 | >10 | 0.2 | >10 | 0.08 | 0.3 | 2.9 |
| FCE 25676 | 1 | 0.002 | 5.6 | 0.02 | 0.02 | 0.1 |
| FCE 25848 | 2.4 | 0.04 | >10 | 0.03 | 0.1 | 7.2 |
| FCE 25452 | 0.9 | 0.009 | >10 | 0.02 | 0.4 | >10 |

IC$_{50}$ μM

In the table cis-Flu. means cis-Flupenthixol; Spip. means Spiperone; Serot. means Serotonin; Ket. means Ketanserine; Praz. means Prazosin and Yohim. means Yohimbine, respectively. The above internal FCE codes refer to the following compounds FCE 25456 = 2-[4-(3-trifluoromethyl-phenyl)-4-hydroxy-piperidin-1-yl]-methyl-4-phenyl-2,3-dihydro-4H-1,4-benzoxazine;

FCE 24867 = 2-(1-phenyl-1,3,8-triazaspiro[4,5]decan-4-one-8-yl)-methyl-4-phenyl-2,3-dihydro-4H-1,4-benzoxazine;

FCE 25895 = (+) 2-(1-phenyl-1,3,8-triazaspiro[4,5]decan-4-one-8-yl)-methyl-4-phenyl-2,3-dihydro-4H-1,4-benzoxazine;

FCE 25896 = (−) 2-(1-phenyl-1,3,8-triazaspiro[4,5]decan-4-one-8-yl)-methyl-4-phenyl-2,3-dihydro-4H-1,4-benzoxazine;

FCE 25676 = 2-(1-phenyl-1,3,8-triazaspiro[4,5]decan-4-one-8-yl)-methyl-4-(4-fluorophenyl)-2,3-dihydro-4H-1,4-benzoxazine;

FCE 25848 = 2-(1-phenyl-1,3,8-triazaspiro[4,5]decan-4-one-8-yl)-methyl-4-phenyl-7-fluoro-2,3-dihydro-4H-1,4-benzoxazine;

FCE 25452 = 2-(1-phenyl-1,3,8-triazaspiro[4,5]decan-4-one-8-yl)-methyl-4-(4-fluorophenyl)-7-fluoro-2,3-dihydro-4H-1,4-benzoxazine.

Table 1 shows clearly that the compounds of the invention have in particular high selective activity in inhibiting the D$_2$ dopamine, 5HT$_2$ serotonine and α$_1$ nor-adrenaline receptor binding.

The activity of the compounds of the present invention on the central nervous system was also evaluated by following for instance the technique of Protais P. et al. (Psychopharmacology, 50, 1 (1976).

According to this experimental framework, the compounds of the invention proved to be very active as antagonists to apomorphine-induced climbing behaviour in mice, i.e. as central dopaminergic antagonists.

Moreover, the compounds of the invention were found to be inactive in a series of tests, carried out so as to find possible undesired side-effects.

For example cataleptic activity was found to be very low in the "bar test" in the mouse (Costall B. et al. Neuropharmacology, 14, 859 (1975), at 6th hour after administration of the test compounds.

The toxicity of the compounds of the invention is negligible, therefore they can be safely used in therapy. Nine hours food deprived mice were treated orally with single administration of increasing doses, then housed and normally fed. The orientative acute toxicity (LD$_{50}$) was assessed on the seventh day after the treatment and resulted, in general, higher than 600 mg/kg. Following Table 2 summarizes the biological data obtained according to the above mentioned tests for some compounds of the present invention; Haloperidol has been evaluated in the same tests for comparative purposes.

TABLE 2

| Compound | Climbing ED$_{50}$ mg/kg/os | Catalepsy ED$_{50}$ mg/kg/os | ED$_{50}$ Catalepsy / ED$_{50}$ Climbing | LD$_{50}$ mg/kg/os |
|---|---|---|---|---|
| FCE 25456 | 2.5 | 20 | 8 | >800 |
| FCE 24867 | 4.5 | 30.8 | 6.8 | >800 |
| FCE 25895 | 3.8 | 61.0 | 16.0 | >800 |
| FCE 25896 | 1.8 | 22.7 | 12.6 | >800 |
| FCE 25676 | 4.9 | 75.0 | 15.3 | >800 |
| Haloperidol | 0.5 | 2.2 | 4.4 | 71 |

The LD$_{50}$ datum for Haloperidol is given according to Il Farmaco-Ed.Sc.1976, 31, 442.

The compounds of the invention can be administered in a variety of dosage forms, e.g. orally, in the form of tablets, capsules, sugar or film coated tablets, liquid solutions or suspensions, rectally, in the form of suppositories, parenterally, e.g. intramuscularly, or by intravenous injection or infusion. The dosage depends on the age, weight, conditions of the patient and administration route; for example for the compound of the invention herein coded as FCE 25895 the dosage adopted for oral administration to adult humans ranges from about 2 to about 100 mg per dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugarcoating, or film coating processes.

The liquid dispersions for oral administration may be e.g. syrups, emulsions and suspensions. The syrups may contain as carriers, for example, saccharose or saccharose with glycerine and/or mannitol and/or sorbitol.

The suspensions and the emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

4-(4-chlorophenyl)-4-hydroxy-piperidine (3 g; 13.3 mmol) is added to a stirred solution of 2-(methane-sulfonyloxy)-methyl-4-phenyl-2,3-dihydro-4H-1,4-benzoxazine (1.76 g; 5.51 mmol) in dimethylformamide (50 ml). The reacting mixture is heated at 90° C. for 3 hours. After cooling, water (150 ml) is added and the product is extracted twice with ethyl acetate (100 ml). The organic layer is washed twice with water (50 ml) and dried over anhydrous sodium sulphate. Evaporation of the solvent gives 2 g of an oily residue which is purified by flash column chromatography on silica gel, by using chloroform/methanol/30% ammonium hydroxide=100/2/0.1 as eluant, thus obtaining 1.7 g of pure oily product (yield 65%).

The pure product is taken up in 10 ml of ethyl acetate and treated, at 0° C., with a gaseous hydrochloric acid saturated ethyl acetate solution, so as to obtain 2-[4-(4-chlorophenyl)-4-hydroxy-piperidin-1-yl]-methyl-4-phenyl-2,3-dihydro-4H-1,4-benzoxazine hydrochloride, as white crystals, m.p. 252°-255° C.

By proceeding analogously, the following compounds, as a free base or as a salt thereof, can be obtained:

2-[4-(4-methoxyphenyl)-piperazin-1-yl]-methyl-4-phenyl-2,3-dihydro-4H-1,4-benzoxazine. 2.5 HCl, m.p. 240°-247° C.;
2-[4-(2-pyrazinyl)-piperazin-1-yl]-methyl-4-phenyl-2,3-dihydro-4H-1,4-benzoxazine. 2 HCl, m.p. 255° C. (dec.);
2-[4-(3-chlorophenyl)-piperazin-1-yl]-methyl-4-phenyl-2,3-dihydro-4H-1,4-benzoxazine. 2 HCl, m.p. 220° C. (dec.);
2-(N-methylaminomethyl)-4-phenyl-2,3-dihydro-4H-1,4-benzoxazine. HCl, m.p. 190° C. (dec.);
2-[4-(2-pyridyl)-piperazin-1-yl]-methyl-4-phenyl-2,3-dihydro-4H-1,4-benzoxazine. 2 HCl, m.p. 120° C. (dec.);
2-(4-phenyl-piperazin-1-yl)-methyl-4-phenyl-2,3-dihydro-4H-1,4-benzoxazine. 2 HCl, m.p. 220°-223° C.;
2-(N-morpholinomethyl)-4-phenyl-2,3-dihydro-4H-1,4-benzoxazine, m.p. 223°-227° C.;
2-(N-propylaminomethyl)-4-phenyl-2,3-dihydro-4H-1,4-benzoxazine. HCl, m.p. 217°-219° C.;
2-aminomethyl-4-phenyl-2,3-dihydro-4H-1,4-benzoxazine. HCl, m.p. 253°-257° C.;
2-[4-(4-chlorophenyl)-4-hydroxy-piperidin-1-yl]-methyl-4-phenyl-7-fluoro-2,3-dihydro-4H-1,4-benzoxazine;
2-[4-(4-chlorophenyl)-4-hydroxy-piperidin-1-yl]-methyl-4-(4-fluorophenyl)-2,3-dihydro-4H-1,4-benzoxazine;
2-[4-(4-chlorophenyl)-4-hydroxy-piperidin-1-yl]-methyl-4-(4-fluorophenyl)-7-fluoro-2,3-dihydro-4H-1,4-benzoxazine;
2-[4-(2-keto-1-benzoimidazolinyl)-piperidin-1-yl]-methyl-4-phenyl-2,3-dihydro-4H-1,4-benzoxazine. HCl, m.p. 185°-188° C.;
2-[4-(2-methoxyphenyl)-piperazin-1-yl]-methyl-4-phenyl-2,3-dihydro-4H-1,4-benzoxazine. 2 HCl, m.p. 235°-238° C.;
2-[4-(2-methoxyphenyl)-piperazin-1-yl]-methyl-4-phenyl-7-fluoro-2,3-dihydro-4H-1,4-benzoxazine;
2-[4-(2-methoxyphenyl)-piperazin-1-yl]-methyl-4-(4-fluorophenyl)-7-fluoro-2,3-dihydro-4H-1,4-benzoxazine;
2-[4-(2-methoxyphenyl)-piperazin-1-yl]-methyl-4-(4-fluorophenyl)-2,3-dihydro-4H-1,4-benzoxazine;
2-[4-(3-trifluoromethyl-phenyl)-4-hydroxy-piperidin-1-yl]-methyl-4-phenyl-2,3-dihydro-4H-1,4-benzoxazine, m.p. 260° C. (dec.), as hydrochloride;
2-[4-(3-trifluoromethyl-phenyl)-4-hydroxy-piperidin-1-yl]-methyl-4-(4-fluorophenyl)-2,3-dihydro-4H-1,4-benzoxazine;
2-[4-(3-trifluoromethyl-phenyl)-4-hydroxy-piperidin-1-yl]-methyl-4-phenyl-7-fluoro-2,3-dihydro-4H-1,4-benzoxazine; and
2-[4-(3-trifluoromethyl-phenyl)-4-hydroxy-piperidin-1-yl]-methyl-4-(4-fluorophenyl)-7-fluoro-2,3-dihydro-4H-1,4-benzoxazine.

EXAMPLE 2

By proceeding according to Example 1 and using suitable acids, the following compounds can be obtained:

2-(N,N-dipropylaminomethyl)-4-phenyl-2,3-dihydro-4H-1,4-benzoxazine fumarate, m.p. 109°-113° C.; and
2-(N,N-dimethylaminomethyl)-4-phenyl-2,3-dihydro-4H-1,4-benzoxazine fumarate, m.p. 109° C. (dec.).

EXAMPLE 3

1-phenyl-1,3,8-triazaspiro[4,5]decan-4-one (2.03 g; 8.8 mmol) is added to a stirred solution of 2-chloromethyl-4-phenyl-2,3-dihydro-4H-1,4-benzoxazine (1.29 g; 4 mmol) in dimethylformamide (20 ml). The reacting mixture is heated at 90° C. for 8 hours. After cooling, water (100 ml) is added and the product is extracted twice with ethyl acetate (80 ml). The organic layer is washed twice with water (30 ml) and dried over anhydrous sodium sulphate. The solid residue, obtained after evaporation of the solvent under reduced pressure, is purified by flash column chromatography on silica gel by using hexane/acetone=9/1 as eluant, thus obtaining 0.7 g of pure 2-(1-phenyl-1,3,8-triazaspiro[4,5]decan-4-one-8-yl)-methyl-4-phenyl-2,3-dihydro-4H-1,4-benzoxazine, yield 37%; m.p. 191°-193° C.

By proceeding analogously the following compounds can be obtained:
2-[4-(4-fluorophenyl)-4-hydroxy-piperidin-1-yl]-methyl-4-phenyl-2,3-dihydro-4H-1,4-benzoxazine, m.p. 105° C.;
2-[4-(4-fluorophenyl)-4-hydroxy-piperidin-1-yl]-methyl-4-phenyl-7-fluoro-4H-1,4-benzoxazine;

2-[4-(4-fluorophenyl)-4-hydroxy-piperidin-1-yl]-methyl-4-(4-fluorophenyl)-2,3-dihydro-1,4-benzoxazine;

2-[4-(4-fluorophenyl)-4-hydroxy-piperidin-1-yl]-methyl-4-(4-fluorophenyl)-7-fluoro-2,3-dihydro-4H-1,4-benzoxazine;

2-[4-(2-keto-1-benzoimidazolinyl)-piperidin-1-yl]-methyl-4-phenyl-7-fluoro-2,3-dihydro-4H-1,4-benzoxazine;

2-[4-(2-keto-1-benzoimidazolinyl)-piperidin-1-yl]-methyl-4-(4-fluorophenyl)-2,3-dihydro-4H-1,4-benzoxazine;

2-[4-(2-keto-1-benzoimidazolinyl)-piperidin-1-yl]-methyl-4-(4-fluorophenyl)-7-fluoro-2,3-dihydro-4H-1,4-benzoxazine;

2-[4-(2-methoxyphenyl)-piperazin-1-yl]-methyl-4-(4-fluorophenyl)-2,3-dihydro-4H-1,4-benzoxazine;

2-(1-phenyl-1,3,8-triazaspiro[4,5]decan-4-one-8-yl)-methyl-4-phenyl-7-fluoro-2,3-dihydro-4H-1,4-benzoxazine, m.p. 198°–200° C.;

2-(1-phenyl-1,3,8-triazaspiro[4,5]decan-4-one-8-yl)-methyl-4-(4-fluorophenyl)-2,3-dihydro-4H-1,4-benzoxazine, m.p. 280° C. (dec.), as hydrochloride, and 2-(1-phenyl-1,3,8-triazaspiro[4,5]decan-4-one-8-yl)-methyl-4-(4-fluorophenyl)-7-fluoro-2,3-dihydro-4H-1,4-benzoxazine, m.p. 288°–292° C., as hydrochloride.

EXAMPLE 4

4-(4-fluorophenyl)-4-hydroxy-piperidine (2.78 g, 14.3 mmol) is added to a stirred solution of 2-(methanesulfonyl)-methyl-4-phenyl-2,3-dihydro-4H-1,4-benzothiazine (2.17 g; 6.5 mmol) in dimethylformamide (60 ml).

The reacting mixture is heated at 90° C. for 3 hours. After cooling, water (150 ml) is added and the product is extracted twice with ethyl acetate (100 ml). The organic layer is washed twice with water (60 ml) and dried over anhydrous sodium sulphate. By evaporating the solvent a solid is obtained, which is purified by flash chromatography on silica gel by using hexane/acetone=9/1 as eluant, thus obtaining 1.17 g of pure 2-[4-(4-fluorophenyl)-4-hydroxypiperidin-1-yl]-methyl-4-phenyl-2,3-dihydro-4H-1,4-benzothiazine, yield 41%.

By proceeding analogously the following compounds can be obtained:

2-[4-(4-fluorophenyl)-4-hydroxy-piperidin-1-yl]-methyl-4-(4-fluorophenyl)-7-fluoro-2,3-dihydro-4H-1,4-benzothiazine;

2-[4-(2-keto-1-benzoimidazolinyl)-piperidin-1-yl]-methyl-4-phenyl-2,3-dihydro-4H-1,4-benzothiazine;

2-[4-(2-keto-1-benzoimidazolinyl)-piperidin-1-yl]-methyl-4-(4-fluorophenyl)-7-fluoro-2,3-dihydro-4H-1,4-benzothiazine;

2-(1-phenyl-1,3,8-triazaspiro[4,5]decan-4-one-8-yl)-methyl-4-phenyl-2,3-dihydro-4H-1,4-benzothiazine; and 2-(1-phenyl-1,3,8-triazaspiro[4,5]decan-4-one-8-yl)-methyl-4-(4-fluorophenyl)-7-fluoro-2,3-dihydro-4H-1,4-benzothiazine.

EXAMPLE 5

Resolution of an acid of formula (V) into the single optical isomers.

To a solution of 4-phenyl-4H-[1,4]-benzoxazine-2-carboxylic acid (20.8 g, 0.08 mol) in 75 ml of methanol (−)ephedrine (13.5 g, 0.08 mol) is added.

The resulting solution is allowed to stand for 1 h: a precipitate is formed which is filtered off. By concentration of the mother liquors a further crop of solid is obtained.

33.4 g of the salt are totally obtained. Resolution is performed by 4 crystallization from $CH_3CN$.

TABLE I

| Crystallization | m.p. (°C.) | $CH_3CN(l)$ | salt obtained (g) | $[\alpha]_D^{25}$ of the salt (methanol) |
|---|---|---|---|---|
| raw material | 139–182 | — | — | −20.3 |
| 1 | 189–9 | 2 | 17.2 | −24.9 |
| 2 | 189–91 | 1.6 | 13.4 | −26.4 |
| 3 | 194–7 | 1.4 | 11.2 | −26.8 |
| 4 | 194–6 | 1.4 | 9.6 | −27.4 |

The mother liquors of the four-crystallizations are collected together, evaporated, taken up with chloroform and washed with 2N HCl. The organic phase is dried and evaporated to give 9.5 g of the free acid which is dissolved in methanol and treated with 6.1 g of (+)ephedrine. After 0.5 hours the solution is evaporated to give an oily residue which, taken up with ether, gives 12.2 g of the (+) salt, which is crystallized twice from $CH_3CN$ (Table II).

TABLE II

| Crystallization | m.p. (°C.) | $CH_3CN(l)$ | salt obtained (g) | $[\alpha]_D^{25}$ of the salt (methanol) |
|---|---|---|---|---|
| raw material | 182–7 | — | — | +24.1 |
| 1 | 192–4 | 1 | 8.9 | +26.4 |
| 2 | 194.6 | 0.8 | 7.4 | +27.3 |

From the (+) and the (−) salts the free optically pure acids are obtained by treatment with HCl, according to usual procedures.

(−) acid $[\alpha]_D^{25}$ (methanol) = −49.5

(+) acid $[\alpha]_D^{25}$ (methanol) = +49.4

EXAMPLE 6

By proceeding analogously to the procedures described in Examples 1 and 3, and using a pure optically active compound of formula (II), the following compounds can be obtained:

(+)2-(1-phenyl-1,3,8-triazaspiro[4,5]decan-4-one-8-yl)-methyl-4-phenyl-2,3-dihydro-4H-1,4-benzoxazine, $[\alpha]_D^{25} = +37.5(CHCl_3)$;

(−)2-(1-phenyl-1,3,8-triazaspiro[4,5]decan-4-one-8-yl)-methyl-4-phenyl-2,3-dihydro-4H-1,4-benzoxazine, $[\alpha]_D^{25} = −37.4(CHCl_3)$;

(+)2-(1-phenyl-1,3,8-triazaspiro[4,5]decan-4-one-8-yl)-methyl-4-(4-fluorophenyl)-2,3-dihydro-4H-1,4-benzoxazine;

(−)2-(1-phenyl-1,3,8-triazaspiro[4,5]decan-4-one-8-yl)-methyl-4-(4-fluorophenyl)-2,3-dihydro-4H-1,4-benzoxazine; and (+)2-[4-(3-trifluoromethyl-phenyl)-4-hydroxy-piperidin-1-yl]-methyl-4-phenyl-2,3-dihydro-4H-1,4-benzoxazine.

EXAMPLE 7

Tablets, each weighing 150 mg and containing 50 mg of the active substance can be manufactured as follows:

| Composition (for 10,000 tablets) | |
|---|---|
| 2-(1-phenyl-1,3,8-triazaspiro[4,5]decan-4-one-8-yl)-methyl-4-phenyl-2,3-dihydro-4H-1,4-benzoxazine | 500 g |
| Lactose | 710 g |

-continued

| Composition (for 10,000 tablets) | |
|---|---|
| Corn starch | 237.5 g |
| Talc powder | 37.5 g |
| Magnesium stearate | 15 g |

2-(1-phenyl-1,3,8-triazaspiro[4,5]decan-4-one-8-yl)-methyl-4-phenyl-2,3-dihydro-4H-1,4-benzoxazine, lactose and a half of the corn starch are mixed; the mixture is then forced through a sieve of 0.5 mm openings. Corn starch (18 g) is suspended in warm water (180 ml).

The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

We claim:

1. A compound having the following formula (I)

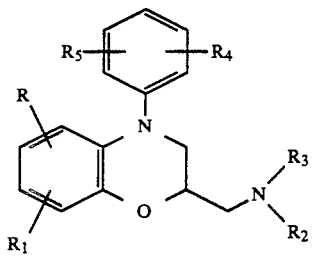

wherein each of R and $R_1$, independently is hydrogen, halogen, hydroxy, $C_1$-$C_6$ alkyl, $C_1$-$C_6$ alkoxy, amino, nitro or trihalo-$C_1$-$C_6$ alkyl;

$R_2$ and $R_3$, taken together with the nitrogen atom to which they are linked, form a piperidine ring substituted by one or two substituents independently chosen from the group consisting of hydroxy, 2-keto-1-benzoimidazolinyl, 1-phenyl-4-keto-5-imidazolidinyl and phenyl unsubstituted or substituted by one or two substituents selected from the group consisting of halogen and trifluoromethyl;

each of $R_4$ and $R_5$, independently is selected from the group consisting of hydrogen, halogen, nitro, amino and trihalo-$C_1$-$C_6$ alkyl; and the pharmaceutically acceptable salts thereof.

2. A compound of formula (I) according to claim 1, wherein each of R and $R_1$, independently, is hydrogen, halogen, hydroxy, $C_1$-$C_6$ alkyl, $C_1$-$C_6$ alkoxy, amino, nitro or trihalo-$C_1$-$C_6$ alkyl;

$R_2$ and $R_3$, taken together with the nitrogen atom to which they are linked, form a piperidine ring substituted by one or two substituents independently chosen from the group consisting of hydroxy, 2-keto-1-benzoimidazolinyl, 1-phenyl-4-keto-5-imidazolidinyl and phenyl unsubstituted or substituted by one or two substituents selected from the group consisting of halogen and trifluoromethyl;

$R_4$ is hydrogen;

$R_5$ is hydrogen, halogen or trifluoromethyl; and the pharmaceutically acceptable salts thereof.

3. A compound of formula (I) according to claim 1, wherein each of R and $R_1$ independently is hydrogen, halogen or trifluoromethyl;

$R_2$ and $R_3$, taken together with the nitrogen atom to which they are linked form a piperidine ring substituted by one or two substituents chosen from hydroxy, 2-keto-1-benzoimidazolinyl, 1-phenyl-4-keto-5-imidazolidinyl and phenyl unsubstituted or substituted by one or two substituents chosen from halogen and trifluoromethyl;

$R_4$ is hydrogen;

$R_5$ is hydrogen, halogen or trifluoromethyl; and the pharmaceutically acceptable salts thereof.

4. A compound of formula (I), according to claim 1, selected from the group consisting of:

2-[4-(4-fluorophenyl)-4-hydroxy-piperidin-1-yl]-methyl-4-phenyl-2,3-dihydro-4H-1,4-benzoxazine;

2-(1-phenyl-1,3,8-triazaspiro[4,5-]decan-4-one-8-yl)-methyl-4-phenyl-2,3-dihydro-4H-1,4-benzoxazine;

2-(1-phenyl-1,3,8-triazaspiro[4,5]decan-4-one-8-yl)-methyl-4-phenyl-7-fluoro-2,3-dihydro-4H-1,4-benzoxazine;

2-(1-phenyl-1,3,8-triazaspiro[4,5]decan-4-one-8-yl)-methyl-4-(4-fluorophenyl)-2,3-dihydro-4H-1,4-benzoxazine;

2-(1-phenyl-1,3,8-triazaspiro[4,5]decan-4-one-8-yl)-methyl-4-(4-fluorophenyl)-7-fluoro-2,3-dihydro-4H-1,4-benzoxazine;

2-[4-(3-trifluoromethyl-phenyl)-4-hydroxy-piperidin-1-yl]-methyl-4-phenyl-2,3-dihydro-4H-1,4-benzoxazine;

2-[4-(3-trifluoromethyl-phenyl)-4-hydroxy-piperidin-1-yl]-methyl-4-(4-fluorophenyl)-2,3-dihydro-4H-1,4-benzoxazine;

2-[4-(3-trifluoromethyl-phenyl)-4-hydroxy-piperidin-1-yl]-methyl-4-phenyl-7-fluoro-2,3-dihydro-4H-1,4-benzoxazine; and 2-[4-(3-trifluoromethyl-phenyl)-4-hydroxy-piperidin-1-yl]-methyl-4-(4-fluorophenyl)-7-fluoro-2,3-dihydro-4H-1,4-benzoxazine;

and the pharmaceutically acceptable salts thereof.

5. A compound of formula (I), or a salt thereof, as claimed in claim 1, wherein said compound is in the form of a single enantiomer.

6. A pharmaceutical composition containing a suitable carrier and/or diluent and, as an active principle, a pharmaceutically effective amount of a compound or salt as claimed in claim 1.

7. A pharmaceutical composition containing a suitable carrier and/or diluent and, as an active principle, a pharmaceutically effective amount of a compound or salt as claimed in claim 2.

8. A pharmaceutical composition containing a suitable carrier and/or diluent and as an active principle, a pharmaceutically effective amount of a compound or salt as claimed in claim 3.

9. A pharmaceutical composition containing a suitable carrier and/or diluent and as an active principle, a pharmaceutically effective amount of a compound or salt as claimed in claim 4.

10. A method of treating psychotic disorders in a patient in need of such treatment, said method comprising administering to the patient a therapeutically effective amount of a compound or salt as claimed in claim 1.

11. A method of treating psychotic disorders in a patient in need of such treatment, said method comprising administering to the patient a therapeutically effective amount of a compound or salt as claimed in claim 2.

12. A method of treating psychotic disorders in a patient in need of such treatment, said method comprising administering to the patient a therapeutically effective amount of a compound or salt as claimed in claim 3.

13. A method of treating psychotic disorders in a patient in need of such treatment, said method comprising administering to the patient a therapeutically effective amount of a compound or salt as claimed in claim 4.

14. A method of treating nausea and vomiting in a patient in need of such treatment, said method comprising administering to the patient a therapeutically effective amount of a compound or salt as claimed in claim 1.

15. A method of treating nausea and vomiting in a patient in need of such treatment, said method comprising administering to the patient a therapeutically effective amount of a compound or salt as claimed in claim 2.

16. A method of treating nausea and vomiting in a patient in need of such treatment, said method comprising administering to the patient a therapeutically effective amount of a compound or salt as claimed in claim 3.

17. A method of treating nausea and vomiting in a patient in need of such treatment, said method comprising administering to the patient a therapeutically effective amount of a compound or salt as claimed in claim 4.

* * * * *